US009518058B2

(12) United States Patent
Eastgate et al.

(10) Patent No.: US 9,518,058 B2
(45) Date of Patent: Dec. 13, 2016

(54) PROCESS FOR THE PREPARATION OF N,N-DICYCLOPROPYL-4-(1,5-DIMETHYL-1H-PYRAZOL-3-YLAMINO)-6-ETHYL-1-METHYL-1,6-DIHYDROIMIDAZO[4,5-D]PYRROLO[2,3-B]PYRIDINE-7-CARBOXAMIDE

(71) Applicant: BRISTOL-MYERS SQUIBB COMPANY, Princeton, NJ (US)

(72) Inventors: Martin D. Eastgate, Trenton, NJ (US); Gregory L. Beutner, Green Brook, NJ (US); Benjamin Cohen, Cranford, NJ (US); Nicolas Cuniere, Belle Mead, NJ (US); Lopa V. Desai, Chesterfield, NJ (US); Monica Fitzgerald, Edison, NJ (US); Qi Gao, Franklin Park, NJ (US); Michael Bryan Hay, Scotch Plains, NJ (US); Michael Joseph Lawler, Mequon, WI (US); Paul C. Lobben, Lawrenceville, NJ (US); Christopher S. Regens, San Francisco, CA (US); Thorsten Rosner, Berkeley Heights, NJ (US); Neil Strotman, Somerset, NJ (US); Carolyn S. Wei, Hoboken, NJ (US); Yi Xiao, Fanwood, NJ (US); Bin Zheng, Kendall Park, NJ (US); Keming Zhu, Highland Park, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/914,330

(22) PCT Filed: Aug. 28, 2014

(86) PCT No.: PCT/US2014/053054
§ 371 (c)(1),
(2) Date: Feb. 25, 2016

(87) PCT Pub. No.: WO2015/031562
PCT Pub. Date: Mar. 5, 2015

(65) Prior Publication Data
US 2016/0229854 A1    Aug. 11, 2016

Related U.S. Application Data

(60) Provisional application No. 61/871,510, filed on Aug. 29, 2013.

(51) Int. Cl.
C07D 471/14    (2006.01)
C07D 207/42    (2006.01)
C07D 403/04    (2006.01)
C07D 231/16    (2006.01)

(52) U.S. Cl.
CPC .......... C07D 471/14 (2013.01); C07D 207/42 (2013.01); C07D 231/16 (2013.01); C07D 403/04 (2013.01)

(58) Field of Classification Search
CPC ..................................................... C07D 471/14
USPC .......................................................... 546/82
See application file for complete search history.

(56) References Cited

U.S. PATENT DOCUMENTS

| 8,202,881 B2 | 6/2012 | Purandare et al. |
| 8,673,933 B2 | 3/2014 | Purandare et al. |
| 2010/0210629 A1 | 8/2010 | Pitts et al. |
| 2011/0059943 A1 | 3/2011 | Purandare et al. |

FOREIGN PATENT DOCUMENTS

WO    WO2008/112695 A1    9/2008

OTHER PUBLICATIONS

G. D. Cuny et al. Structure-activity relationship study of bone morphogenic protein (BMP) signaling inhibitors, Bioorganic and Medicinal Chemistry Letters, vol. 18, Jun. 27, 2008 pp. 4388-4392.

*Primary Examiner* — Taofiq A Solola
(74) *Attorney, Agent, or Firm* — Elliott Korsen

(57) ABSTRACT

The invention relates to an improved process for synthesizing N,N-dicyclopropyl-4-(1,5-dimethyl-1H-pyrazol-3-ylamino)-6-ethyl-1-methyl-1,6-dihydroimidazo[4,5-d]pyrrolo[2,3-b]pyridine-7-carboxamide of the formula: (I) Compound (I) is currently in clinical trials for the treatment of myeloproliferative disorders, such as polycythaemia vera, thrombocythaemia and primary myelofibrosis.

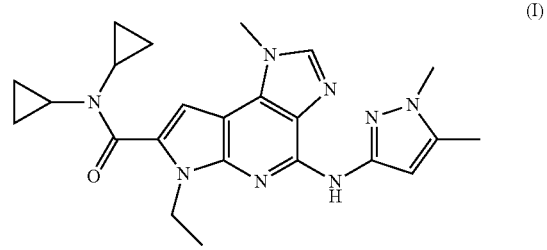

(I)

9 Claims, No Drawings

PROCESS FOR THE PREPARATION OF N,N-DICYCLOPROPYL-4-(1,5-DIMETHYL-1H-PYRAZOL-3-YLAMINO)-6-ETHYL-1-METHYL-1,6-DIHYDROIMIDAZO[4,5-D]PYRROLO[2,3-B]PYRIDINE-7-CARBOXAMIDE

CROSS REFERENCE TO RELATED APPLICATIONS

This application claims priority from U.S. Provisional Application No. 61/871,510 filed Aug. 29, 2013, the disclosure of which is incorporated herein by reference in its entirety.

FIELD OF THE INVENTION

The invention generally relates to several improved processes for the preparation of N,N-dicyclopropyl-4-(1,5-dimethyl-1H-pyrazol-3-ylamino)-6-ethyl-1-methyl-1,6-dihydroimidazo[4,5-d]pyrrolo[2,3-b]pyridine-7-carboxamide, a JAK2 inhibitor currently in clinical trials for the treatment of myeloproliferative disorders, which include polycythaemia vera, thrombocythaemia and primary myelofibrosis.

BACKGROUND OF THE INVENTION

There are disclosed significantly improved processes for the preparation of N,N-dicyclopropyl-4-(1,5-dimethyl-1H-pyrazol-3-ylamino)-6-ethyl-1-methyl-1,6-dihydroimidazo[4,5-d]pyrrolo[2,3-b]pyridine-7-carboxamide, of formula I:

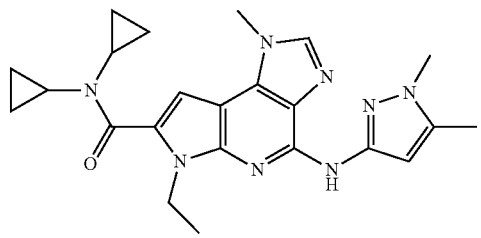

(I)

Compound I, compositions comprising Compound I, and methods of using Compound I are disclosed in U.S. Pat. No. 8,202,881 B2, which is assigned to the present assignee and is incorporated herein by reference in its entirety.

SUMMARY OF THE INVENTION

In a first aspect, the invention provides a process for preparing Compound I of the formula:

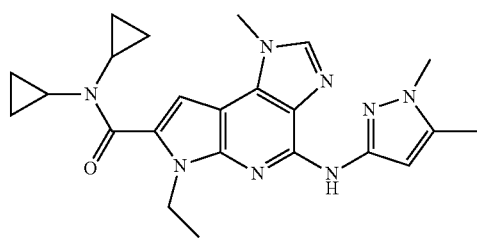

(I)

comprising the steps of
a) reacting Compound 1 of the formula

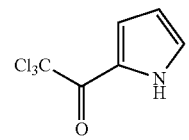

Compound 1 with a halogenating agent, such as NBS, in a suitable solvent to afford Compound 2 of the formula

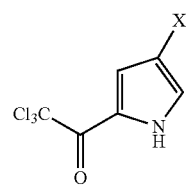

Compound 2 wherein X is Cl, Br or I;
b) reacting Compound 2 with an alcohol, and optionally a base, to afford Compound 3 of the formula

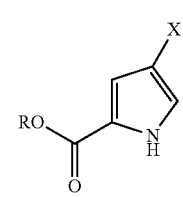

Compound 3 wherein
R is Me, Et, i-Pr, n-Pr, n-Bu, sec-Bu or t-Bu; and
X is as defined above;
c) subsequently reacting Compound 3 with a nitrating agent to afford Compound 4 of the formula

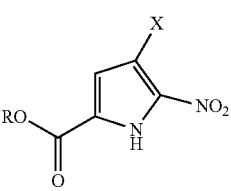

Compound 4 d) reacting Compound 4, first, with an ethylating agent to afford Compound 5 of the formula

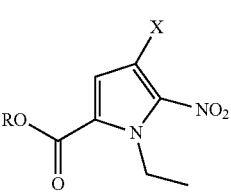

Compound 5 wherein R and X are as previously defined
and, subsequently with a suitably substituted imidazole of the formula,

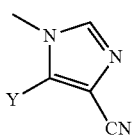
Compound 33 wherein
Y is H, Cl, Br, I or —B(OR')$_2$;
R' is Me, Et, i-Pr, n-Pr, n-Bu, sec-Bu, t-Bu, —(CH$_2$)$_n$ or —C(Me)$_2$C(Me)$_2$-; and
n is 2, 3, 4 or 5;
in the presence of a suitable catalytic metal, a ligand, an inorganic salt and optionally an organic base, to afford Compound 6 of the formula

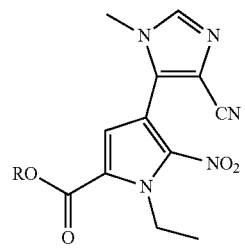
Compound 6 wherein R is as previously defined;
e) which is then reacted with hydrogen in the presence of a suitable catalytic metal
and optionally a base, to afford Compound 7 of the formula

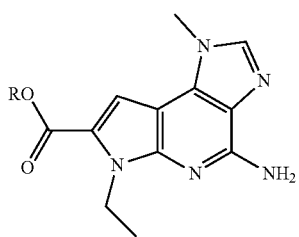
Compound 7 wherein R is as defined above;
f) which is reacted with the Compound 24 of the formula

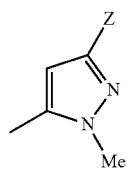
Compound 24 wherein Z is Cl, Br, I, —OP(O)(OR")$_2$ or —OS(O)CF$_3$;
in the presence of a suitable metal, a ligand, and base, to afford Compound 26 of the formula

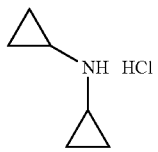
Compound 26 wherein R" is Ph or t-Bu and M is Li, Na, K, Cs, Rb, Mg or Ca;
g) which is reacted with Compound 27 of the formula Compound 27

NH HCl in a the presence of a suitable activator, a suitable solvent, such as DCM, and optionally a base, to afford Compound I.

The term "ligand" as used herein refers to a phosphine derivative that ligates palladium such as a mono or bidentate aryl or alkyl phosphine, which is capable of complexing a palladium atom. The term is well known to one skilled in the particular art.

In a second aspect, there is provided a process for the preparation of Compound 7 of the formula:

Compound 7 which comprises:
a) reacting Compound 1 of the formula

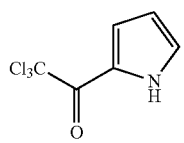
Compound 1 with a halogenating agent, such as NBS, in a suitable solvent to afford Compound 2 of the formula

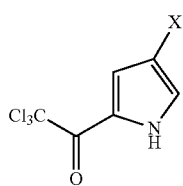
Compound 2 b) reacting Compound 2 with base and an alcohol to afford Compound 3 of the formula

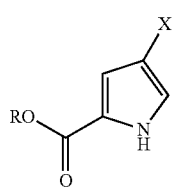
Compound 3 c) reacting Compound 3 with an ethylating agent to afford Compound 14

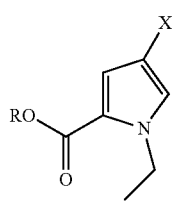
Compound 14 d) reacting Compound 14 with an appropriate diboron reagent, in the presence of a catalytic metal, ligand and base to afford Compound 15

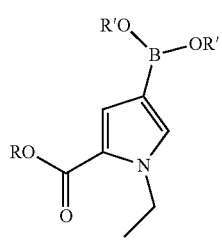
Compound 15 e) reacting Compound 15 with Compound 33 of the formula,

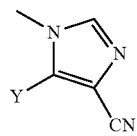
Compound 33 in the presence of a catalytic metal, ligand and an appropriate base, to afford Compound 16

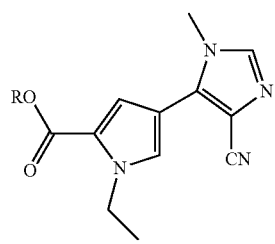
Compound 16 f) reacting Compound 16 with a suitable hydroxylamine derivative to afford Compound 17

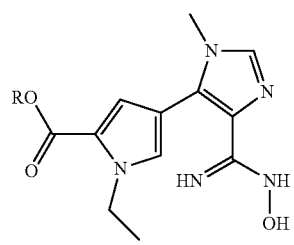
Compound 17 g) and, reacting Compound 17 with a suitable metal, hydrogen and, optionally, an activating group, to afford Compound 7

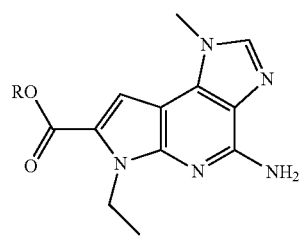
Compound 7 wherein:
R, R' and X are as previously defined.
In a preferred embodiment, R' is —C(Me)$_2$C(Me)$_2$-.
In a third aspect, the invention provides another process for preparing Compound 7 of the formula:

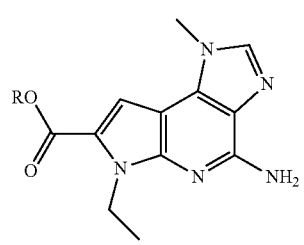
Compound 7 which comprises
a) reacting Compound 1 of the formula

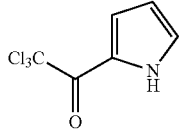

Compound 1 with a halogenating agent, such as NBS, in a suitable solvent, to afford Compound 2 of the formula

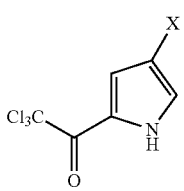

Compound 2 b) reacting Compound 2 with base and an alcohol to afford Compound 3 of the formula

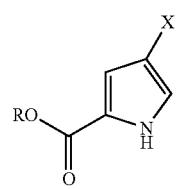

Compound 3 c) reacting Compound 3 with a nitrating agent to afford Compound 4 of the formula

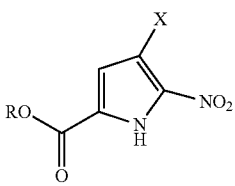

Compound 4 d) reacting Compound 4, first, with an ethylating agent to afford Compound 5 of the formula

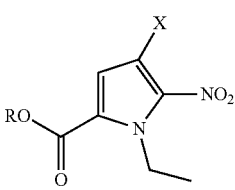

Compound 5

And, subsequently with Compound 33 of the formula,

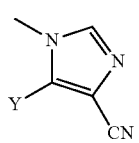

Compound 33 in the presence of an appropriate ligand and an appropriate base to afford Compound 6

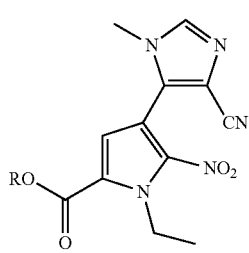

Compound 6 e) and, reacting Compound 6 with hydrogen, a metal catalyst and optionally a base, to afford Compound 7

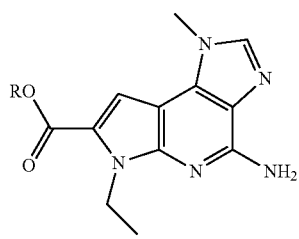

Compound 7 wherein R, X and Y are as previously defined.

In a fourth aspect, there is provided a process for the preparation of Compound 26 of the formula

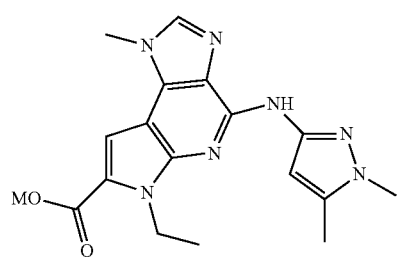

Compound 26 which comprises:

a) reacting Compound 7 of the formula

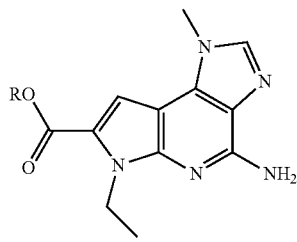
Compound 7 with Compound 24 of the formula

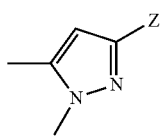
Compound 24 to provide Compound 25,

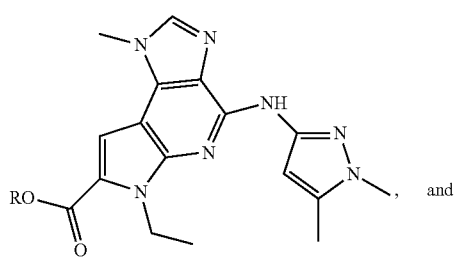
Compound 25 b) reacting Compound 25 with an aqueous inorganic base in a suitable solvent to prepare Compound 26

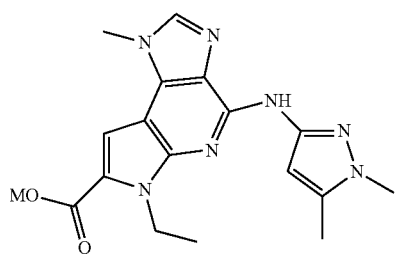
Compound 26 wherein R and M are as previously defined; and Z is Cl, Br, I, —OP(O)(OR')$_2$ or —OS(O)CF$_3$.

In a fifth aspect, there is provided a process for the preparation of Compound 26

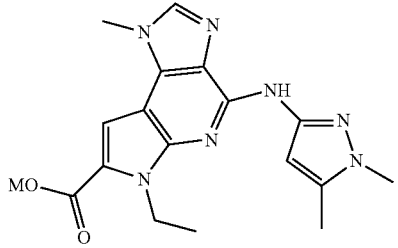
Compound 26 which comprises a) reacting Compound 7 of the formula

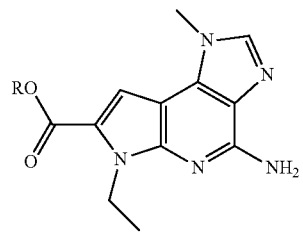
Compound 7 with a suitable strong base in water, a metal catalyst, a ligand and Compound 24 (or salt forms thereof) of the formula

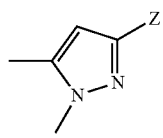
Compound 24 and subsequently treating the solution with a metal salt to provide Compound 26, wherein R, Z and M are as previously defined.

A further aspect of the invention provides a compound of formula I by reacting Compound 26

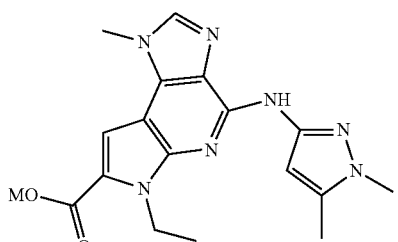
Compound 26 where M is as defined above, with an activator, optionally a catalyst, in the presence of base and dicyclopropylamine (optionally as its hydrochloride salt) to prepare Compound I.

A further aspect of the invention provides basic salt forms of the pyrrole derivative with amine derivatives

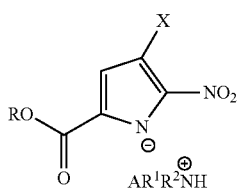

wherein

R and X are as previously defined, A is H, $NH_2$, OH or $R^1$;

$R^1$ and $R^2$ are independently $C_1$-$C_5$ alkyl, benzyl, allyl, —$(CH_2CH_2)_2O$, —$(CH_2CH_2)_3N$, and other simple amine bases such as, TEA, DBU, DIPEA, DABCO, DCHA, tetramethyl guanidine, ammonia, hydrazine, morpholine, DMAP, tetramethyl piperidine and dibenzylamine.

In a preferred embodiment, R is Et, A is H, X is Br and $R^1$ and $R^2$ are both benzyl.

Another aspect of the invention provides Compound 10a of the formula

Compound 10a

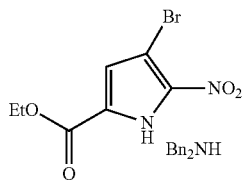

Another aspect of the invention provides Compound 5 of the formula

Compound 5

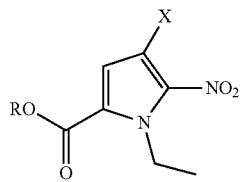

wherein R and X are as previously defined.

Another aspect of the invention provides Compound 13 of the formula as its free base, or acidic salt which is Compound 13

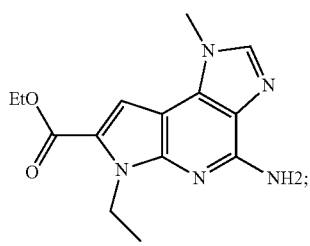

Compound 13a

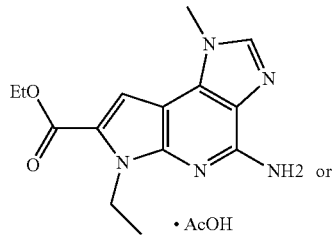

Compound 13b

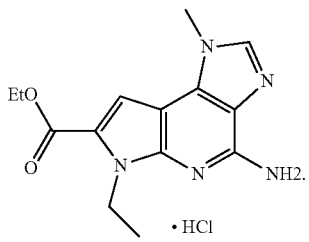

Another aspect of the invention provides acidic salt forms of Compound 29

Compound 29

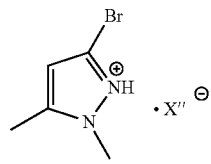

where X" is Cl, Br or $CF_3SO_3$.

Another aspect of the invention provides compound 31 of the formula as its free form, hydrate or hydrated ethanol solvate Compound 31

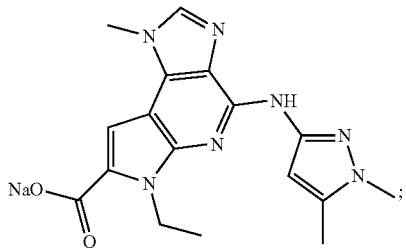

Compound 31a

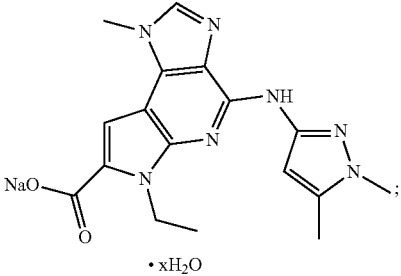

-continued

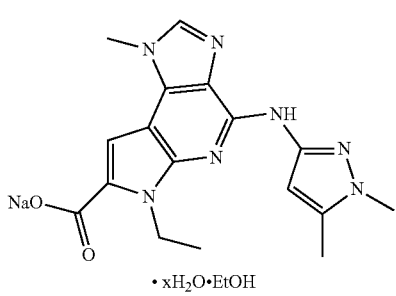
Compound 31b

Another aspect of the invention provides a method for nitrating Compound 9 of the formula

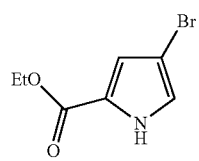
Compound 9 which comprises combining a metal salt of nitric acid selected from $NaNO_3$, $KNO_3$ or $LiNO_3$, with $SO_3$.pyridine complex, in the presence of the respective metal sulfate salt selected from $Na_2SO_4$, $Li_2SO_4$ or $K_2SO_4$, and metal bisulfate salt selected from $NaHSO_4$, $LiHSO_4$ or $KHSO_4$, in a suitable solvent, such as MeCN, to afford Compound 10 of the formula

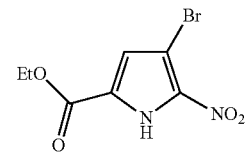
Compound 10

Another aspect of the invention provides a method for coupling Compound 11

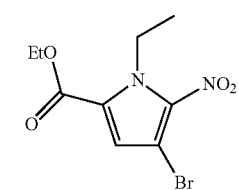
Compound 11 to Compound 28 of the formula

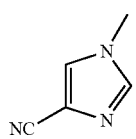
Compound 28 which comprises treating Compound 11 with a suitable palladium source such as $PdCl_2$ (or a pre-ligated version), a phosphine ligand such as Xantphos and a suitable potassium source such as potassium pivalate (PivOK) and optionally an organic base such as Hunig's base, to afford Compound 12 of the formula

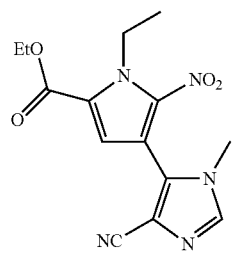
Compound 12

Another aspect of the invention provides a method for coupling amine derivative Compound 7 of the formula

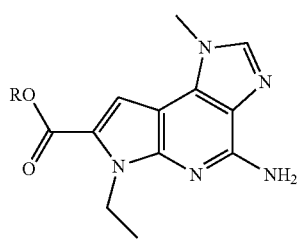
Compound 7 to Compound 29 of the formula

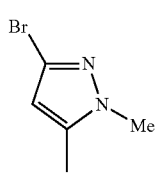
Compound 29 in the presence of a suitable palladium source, a ligand and a base in a suitable solvent (such as tAmylOH).

Another aspect of the invention provides a method of coupling Compound 31 of the formula

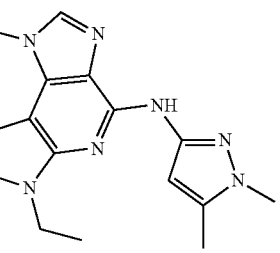
Compound 31 to Compound 27 of the formula

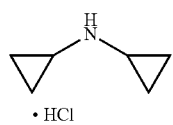

which comprises treating Compound 31 with DPPCl in the presence of base, then reacting Compound 27 in the presence of DMAP to afford Compound I.

Another aspect of the invention provides a method of coupling Compound 31 to Compound 27 of the formula by treating Compound 31 with DMC, followed by treatment with Compound 27 in the presence of base DMAP, to afford Compound I.

Another aspect of the invention provides Compound I prepared by the processes described herein.

A final aspect of the invention provides a method for treating a myeloproliferative disorder, comprising administering to a mammalian species, preferably a human, in need thereof, a therapeutically effective amount of Compound I, wherein Compound I is prepared utilizing the novel process steps of the invention.

The processes of the invention have several important advantages over prior syntheses of Compound I. In particular, due to the short sequence of chemical steps, high yields and process improvement, the throughput, cycle-time and overall yield have been dramatically improved. Additionally, the process consistently provides Compound I in high quality for use as a pharmaceutical API.

What is now needed in the art are new methods of making the pyrrolopyridine compound, which is useful against myeloproliferative diseases, both in terms of overall yield and material throughput.

DETAILED DESCRIPTION OF THE INVENTION

The following schemes illustrate the improved synthetic steps of the invention. These Schemes are illustrative and are not meant to limit the possible techniques one skilled in the art may use to manufacture compounds disclosed herein.

As shown below in Scheme 1, the general preparation of compound 7 is described. Trichloroacetyl pyrrole (Compound 1) is reacted with a halogenating agent to give the C4-bromo pyrrole (Compound 2). Alcoholysis occurs in the presence of an alcohol and base to generate ester (Compound 3), which can be selectively nitrated through contact with an appropriate nitrating agent (defined as a species that generates $NO_2^+$), yielding C5-nitro pyrrole (Compound 4). Compound 4 can be isolated as its free form, or optionally as a salt with an appropriate base. Ethylation with an appropriate alkylating agent generates the N-ethyl pyrrole (Compound 5), which in the presence of an imidazole, base, palladium and an appropriate phosphine ligand, will undergo a coupling process to form Compound 6. Reduction of the nitro-group of Compound 6 in the presence of hydrogen, a metal catalyst and optionally a base will produce Compound 7.

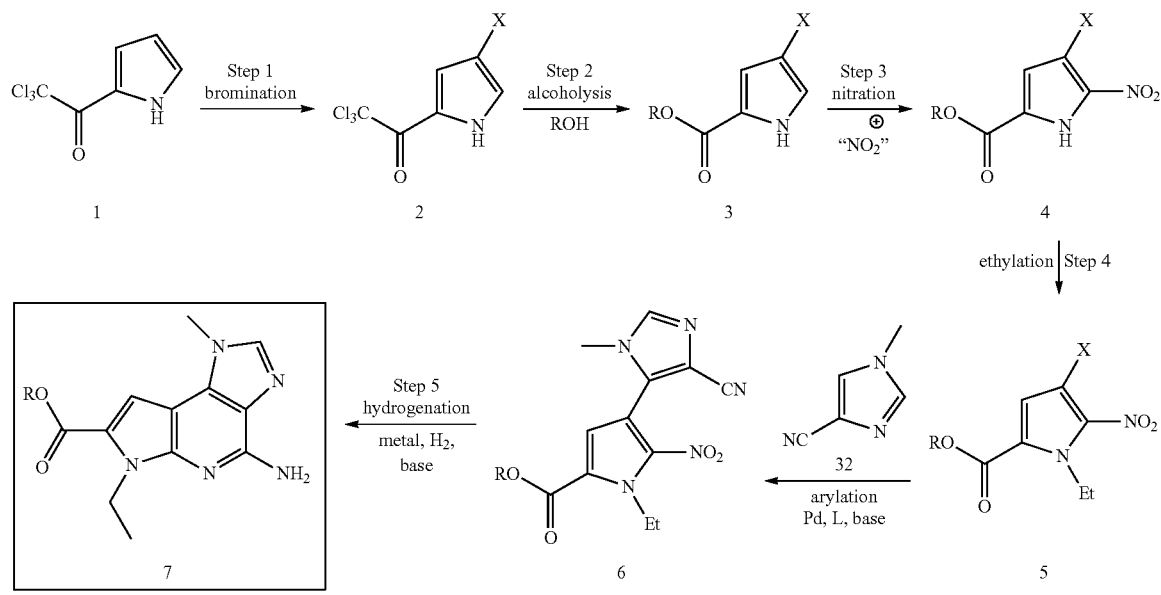

Scheme 1

As shown below in Scheme 2, the preparation of Compound 13 is described. Trichloroacetyl pyrrole is treated with NBS in acetonitrile to produce Compound 8. Treatment with sodium ethoxide in EtOH yields the ethyl ester Compound 9. This may be treated with a range of nitrating systems, in this example, $NaNO_3/SO_3 \cdot Py$, to generate nitro-pyrrole Compound 10, which can be isolated directly or as a salt form with an appropriate base, preferably dibenzylamine. Ethylation with ethyl iodide generates Compound 11 which may be isolated, or optionally telescoped directly into the arylation with Compound 32. Arylation proceeds in the presence of palladium, Xantphos, potassium pivylate and Hunig's base to generate Compound 12. Hydrogenation in the presence of Pt/C followed by cyclization with NaOEt yields Compound 13.

Scheme 2

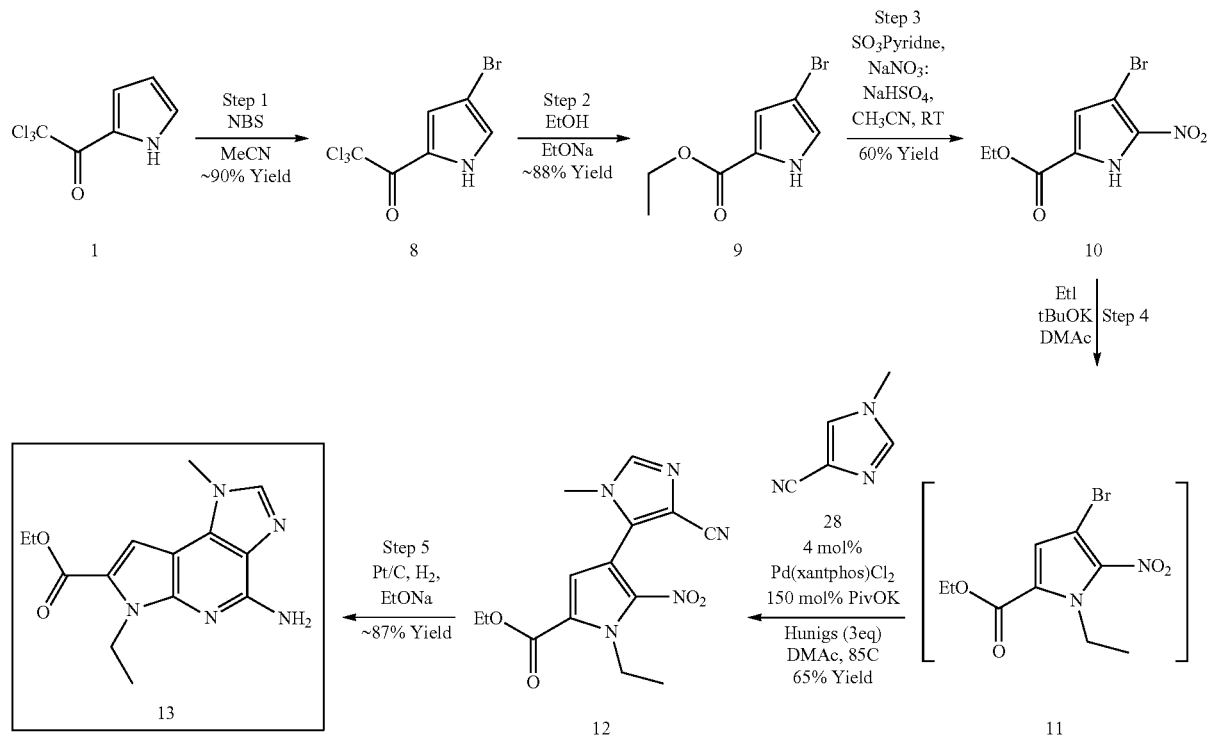

Another process of the invention is disclosed in Scheme 3 shown below. Compound 14 is prepared from Compound 3 in the presence of an alkylating agent. Treatment with a suitable diboron reagent produces Compound 15, which can then be coupled with a suitably functionalized imidazole derivative to yield Compound 16. Aminolysis with a suitable nitrogen donor produces Compound 17, which can cyclize under appropriate conditions to produce Compound 7.

Scheme 3

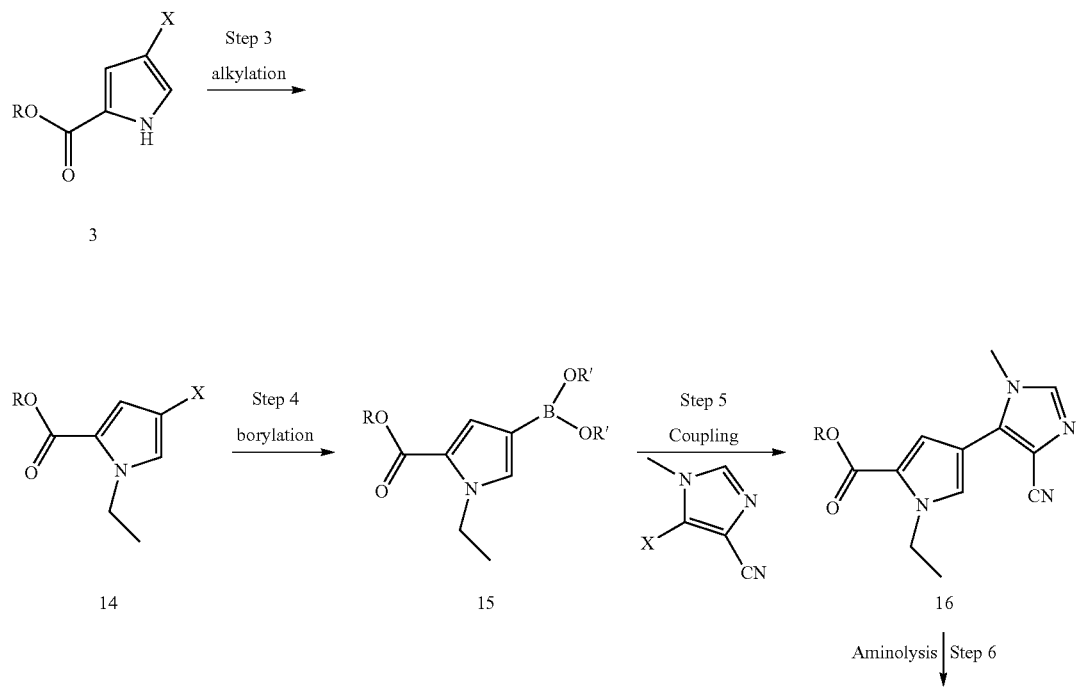

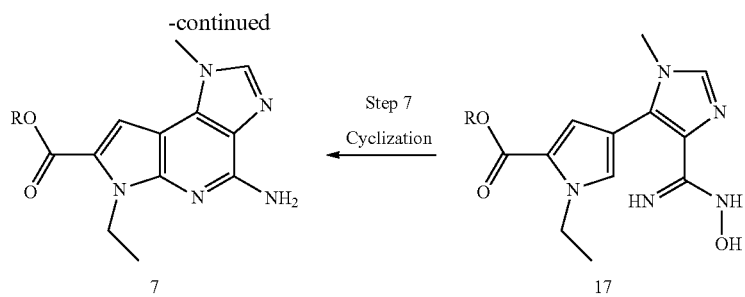

As shown below in Scheme 4, ethylation of Compound 9 with ethyl iodide produces Compound 18. This may be directly reacted with dipinacol-diboron in the presence of Pd(OAc)₂ and tricyclohexylphosphin hexafluorophosphate and tetramethylammonium acetate to yield Compound 19. Subsequent coupling with 5-Br-imidazole derivative yields Compound 20. Treatment with hydroxylamine hydrochloride in the presence of triethylamine yields the Compound 21. Subsequent cyclization with Piv₂O in the presence of PRICAT™ and hydrogen yields Compound 13.

Scheme 4

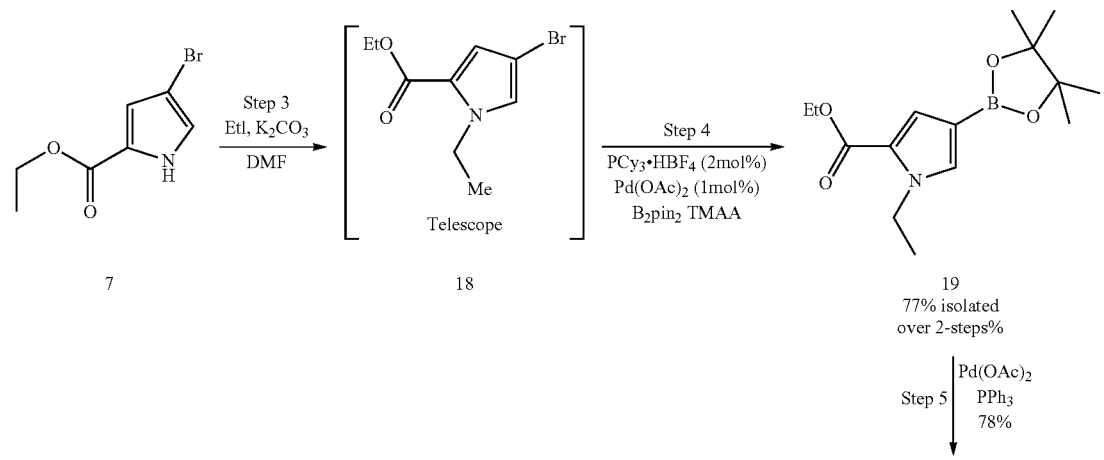

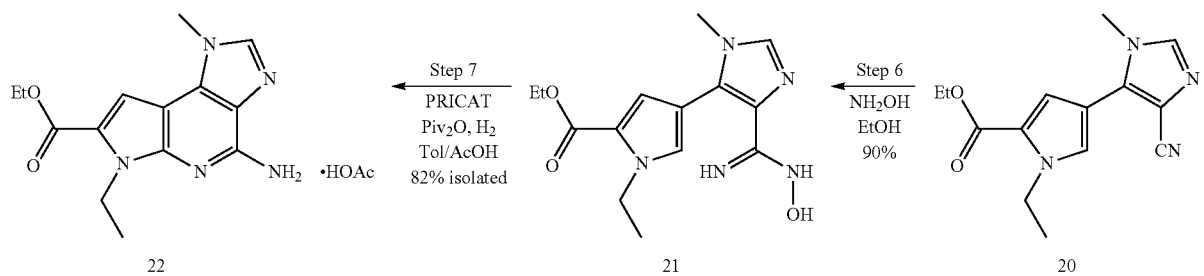

As shown below in Scheme 5, Compound 23 may be converted to Compound 26 by two pathways. In one option, Compound 23 can be treated with palladium, ligand and a mild base to prepare Compound 25. Reaction of Compound 25 with a metal hydroxide produces Compound 26.

Alternately, Compound 23 can be treated with palladium and ligand in the presence of a soluble hydroxide base, followed by treatment with the metal counter-ion to prepare Compound 26 directly. Once Compound 26 is formed, it can be coupled to Compound 27 to form compound I.

Scheme 5

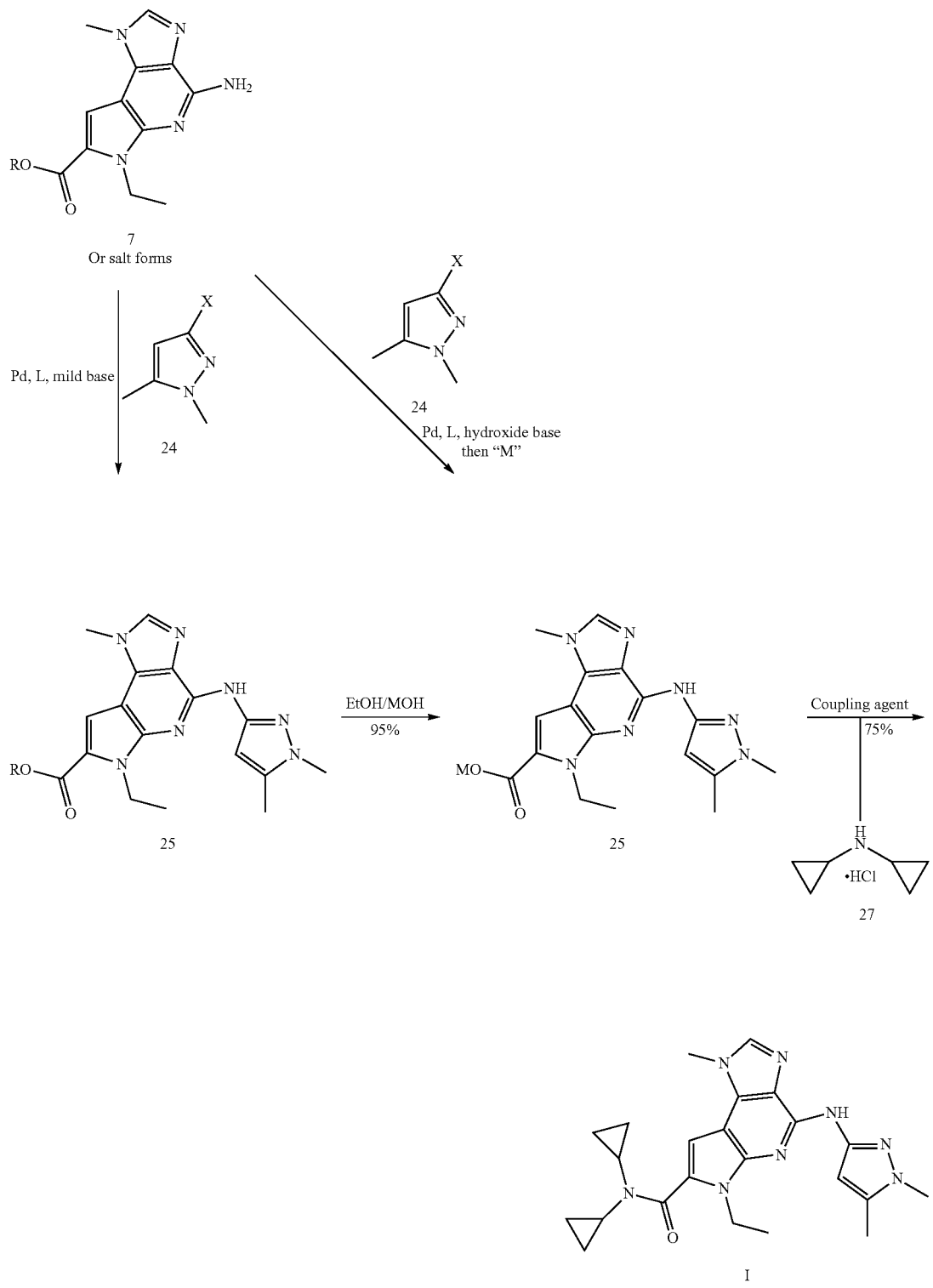

EXAMPLES

The invention will now be further described by the following working example(s), which are preferred embodiments of the invention. All temperatures are in degrees Celsius (° C.) unless otherwise indicated. These examples are illustrative rather than limiting and it is to be understood that there may be other embodiments that fall within the spirit and scope of the invention as defined by the claims appended hereto.

For ease of reference, the following abbreviations may be used herein.

ABBREVIATIONS

| | |
|---|---|
| ACN | acetonitrile |
| AcOH | acetic acid |
| Ac$_2$O | acetic anhydride |
| ADDP | 1,1'-(azodicarbonyl)dipiperidine |
| aq. | aqueous |
| Bn | benzyl |
| Boc | t-butyl carbamate |
| Boc$_2$O | di-t-butyl dicarbonate |
| Bu | butyl |
| Cbz | benzyl carbamate |
| conc. | concentrated |
| DCE | dichloroethane |
| DCM | dichloromethane |
| DIAD | diisopropyl azodicarboxylate |
| DIEA | diisopropylethylamine |
| DIPEA | N,N-diisopropylethylamine |
| DMAP | 4-N,N-dimethylaminopyridine |
| DMF | dimethyl formamide |
| DMSO | dimethyl sulfoxide |
| DMT-MM | 4-(4,6-dimethoxy-1,3,5-triazin-2-yl)-4-methylmorpholinium chloride |
| EDC | 1-(dimethylaminopropyl)-3-ethylcarbodiimide hydrochloride |
| eq. | equivalents |
| Et | ethyl |
| EtOAc | ethyl acetate |
| EtOH | ethanol |
| Et$_2$O | diethyl ether |
| Et$_3$N | triethylamine |
| Fmoc | 9-fluorenylmethyl carbamate |
| h | hour(s) |
| HATU | O-(7-azabenzotriazol-1-yl)-N,N,N',N'-tetramethyluronium hexafluorophosphate |
| HOAt | 1-hydroxy-7-azabenzotriazole |
| HPLC | high pressure liquid chromatography |
| i-PrOH | isopropanol |
| KOAc | potassium acetate |
| LAH | Lithium aluminum hydride |
| LR | Limiting reagent |
| min | minute(s) |
| Me | methyl |
| MeCN | acetonitrile |
| MeOH | methanol |
| Me$_2$NH | dimethyl amine |
| NaHMDS | sodium bis(trimethylsilyl)amide |
| Na(OAc)$_3$BH | sodium triacetoxyborohydride |
| n-BuLi | n-butyl lithium |
| NCS | N-chlorosuccinimide |
| NMM | N-methylmorpholine |
| NMP | n-methylpyrrolidinone |
| NMR | nuclear magnetic resonance |
| OTf | trifluoromethylsulfonyloxy |
| Pd/C | palladium on carbon |
| Pd(dppf)$_2$Cl$_2$ | [1,1'-bis(diphenylphosphino)ferrocene]dichloropalladium(II) |
| Pd(OAc)$_2$ | palladium acetate |
| Pd(PPh$_3$)$_4$ | tetrakis(triphenylphosphine)palladium |
| Pd$_2$(dba)$_3$ | tris(dibenzylideneacetone)dipalladium(0) |
| Ph | phenyl |
| PhMe | toluene |
| Ph$_2$TfN | 1,1,1-trifluoro-N-phenyl-N-(trifluoromethyl)sulfonyl methanesulfonamide |
| PPh$_3$ | triphenyl phosphorus |
| rt/RT | room temperature |
| sat. | saturated |
| t-Bu | tertiary butyl |
| t-BuOH | tertiary butanol |
| TFA | trifluoroacetic acid |
| Tf$_2$O | trifluoromethylsulfonic anhydride |
| THF | tetrahydrofuran |
| TMAA | tetra-methyl ammonium acetate |
| TMS | trimethylsilyl |
| TsO | p-toluenesulfonyl |
| Xantphos | 4,5-bis(diphenylphosphino)-9,9-dimethylxanthane |

Example 1

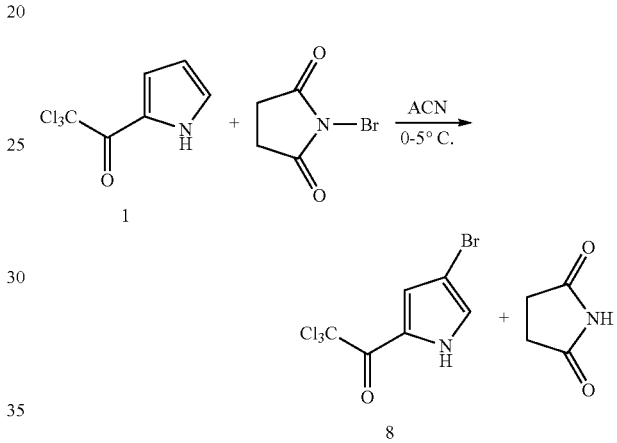

A solution of Compound 1 in acetonitrile (1238.0 kg, 264.9 kg after correction) was charged into a 5000 L glass-lined reactor at a temperature of 20-30° C. The mixture was added with stirring over about 2 h and then cooled to 0° C. NBS (221.8 kg) was charged into the mixture at intervals of 20-30 min at 0-20° C. The mixture was cooled to 0-5° C. and reacted until the content of Compound 8 was ≤1.0%. Additional NBS (4.0 kg) was charged into the mixture at 0-20° C. The mixture was reacted over 3 h until the content of Compound 8 was ≤1.0%. Purified water (2650.0 kg) was added over about 1.5-2.5 h at 0-20° C. The mixture was cooled to 0-5° C. and then stirred for about 1 h for crystallization. The mixture was filtered and the filter cake was rinsed with water.

Example 2

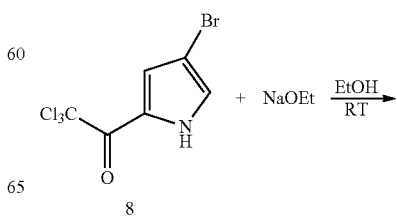

25
-continued

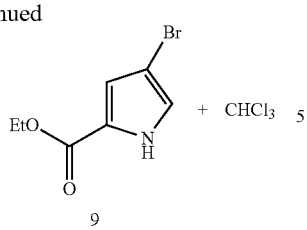

26
-continued

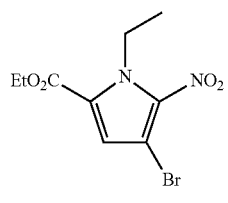

While maintaining the temperature at 20-30° C., anhydrous ethanol (950.0 kg) was charged into a 3000 L glass-lined reactor followed by Compound 8 (342.7 kg). The mixture was cooled to 0-5° C. over about 2 h. Sodium alcoholate solution in ethanol (21%, 36.4 kg) was added dropwise over about 1-1.5 h at 0-5° C. The reaction mixture was then heated to about 25-30° C. and tested until the content of Compounds 8/9 was ≤1.0%. The reaction mixture was concentrated at a temperature ≤50° C. until about 1.3-1.4 volume of Compound 8 was left. The concentrated mixture was cooled at 25-30° C. The mixture was quenched into cooled water (3427.0 kg) over about 2 h. After addition, the mixture was stirred at 0-5° C. over about 2 h for crystallization. The mixture was filtered and the filter cake was rinsed. The solid was dried at 30-40° C. over 40-45 h to afford 234.3 kg of Compound 9, 99.9% purity and 91.3% yield.

Compound 10 (1.0 eq) and TBABr (1.0 eq) were added to a biphasic mixture of toluene (8 L/kg 10) and potassium carbonate (1.5 eq) in water (5 L/kg 10). The batch temperature was held at 25° C. The resulting triphasic slurry was heated to 60-65° C. and diethylsulfate (1.5 eq, in a solution of toluene 2 L/kg 10) was slowly added over ~1 h. The reaction was aged until less than 1 RAP of Compound 10 (10:11) remained. The resulting homogeneous biphasic mixture was cooled to 20° C. and the lean aq. phase was removed. The rich organic phase was washed with water (2×7 L/kg 10) and concentrated to 6 mL/g 10. The concentrated stream was dried via azeotropic, constant volume distillation with toluene until the water content of the stream was <0.1 wt %. The resulting stream was telescoped into the subsequent direct arylation reaction.

Example 3

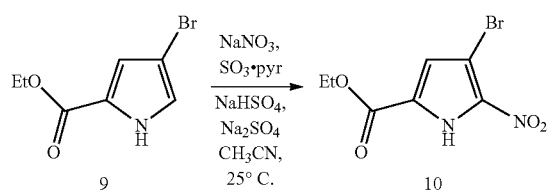 [SMILES: CCOC(=O)c1cc(Br)c[nH]1 ; CCOC(=O)c1cc(Br)c([N+](=O)[O-])[nH]1]

A mixture of NaNO₃, NaHSO₄, and Na₂SO₄ in CH₃CN is wet-milled to constant particle size of ~50 micron. To the slurry of inorganic salts is added SO₃·pyridine and Compound 9. The reaction mixture is agitated at 25° C. until 90-95% conversion is achieved. The reaction is quenched with aqueous sodium hydroxide and the spent inorganic salts are removed by filtration. The filtrate is passed through a carbon pad and distilled under constant volume distillation and diluted with water to a target 15 volumes/kg of Compound 9 and a target ratio 1.0:2.0 vol/vol MeCN to water. The resulting solids are deliquored, washed, and dried to afford Compound 10.

Example 4

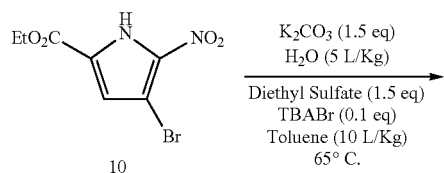

Example 5

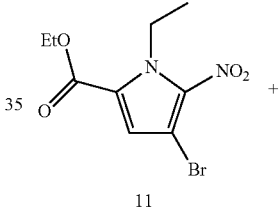

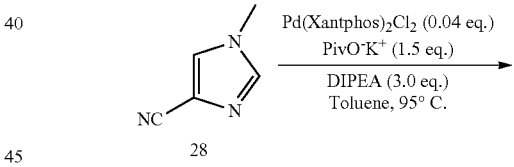

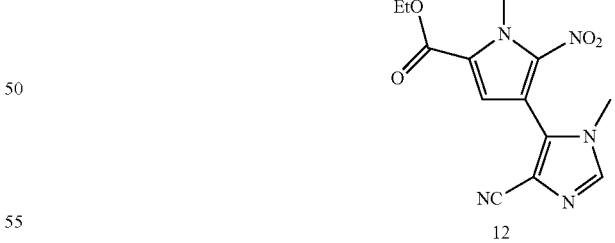

To the toluene stream of Compound 11, with potassium pivalate (1.5 equiv.) was charged, followed by DIPEA (3 eq.), Compound 28 (3 eq.) and Pd(Xantphos)Cl₂ (0.04 eq.). The vessel was evacuated to <200 torr and backfilled with nitrogen (3×) followed by heating to 95° C. until residual Compound 11 was less than 1 RAP (11:12). The reaction mixture was cooled to 25° C. and diluted with ethyl acetate (15 mL/g vs input pyrrole) and aq. N-acetylcysteine (0.2 eq., 5 wt % solution, 1.8 mL/g vs. input pyrrole) and heated to 50° C. for 1 h. The biphasic mixture was cooled to 25° C.

The lower aqueous layer was removed. The ethyl acetate stream was washed with water (2×7 mL/g vs. input pyrrole). The rich organic phase was polish filtered followed by a vessel/polish filter rinse with ethyl acetate (2 mL/g vs. input pyrrole). The rich organic stream was concentrated to 4 mL/g vs. input pyrrole via vacuum distillation, while maintaining the batch temperature above 50° C. If spontaneous nucleation did not occur, Compound 12 seeds (1 wt %) were charged, followed by aging for 30 min at temperature. MTBE (5 mL/g vs. 11) was charged to the slurry over 1 hour while maintaining the batch temperature above 40° C., followed by aging at 40° C. for 1 h. The slurry was cooled to 0° C. over 6 h and aged at 0° C. for 6 h. The slurry was filtered and washed with EtOAc:Toluene:MTBE (1.5:1.0:1.5, 2 mL/g vs. input 11). The wet cake was dried (50° C., 100 torr) until LOD was <1 wt %.

Example 6

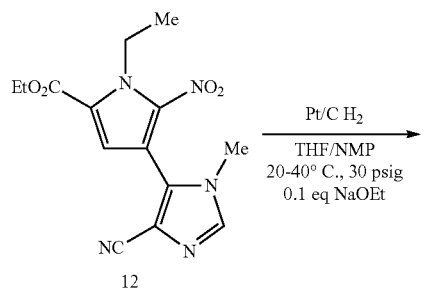

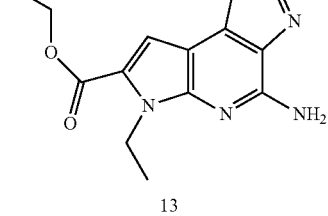

Compound 12 (1 eq., limiting reagent (LR)) is dissolved in THF/NMP (20 Vol wrt LR, 9/1 ratio) and submitted to hydrogenation using 10 wt % (wrt LR) Pt/C (5 wt %) at 25 to 40° C. for 5-10 h. The reaction containing the corresponding amine is filtered. The rich organic stream is concentrated to Compound 12 Vol (wrt LR) and subjected to 0.1 eq of 21 wt % NaOEt/EtOH for 5 h at 20-25° C., upon which Compound 13 forms. The stream is cooled to 0-10° C., and water (5 L/Kg, wrt to LR) is added and then filtered to isolate Compound 13. The product is dried at 50° C. under vacuum.

Example 7

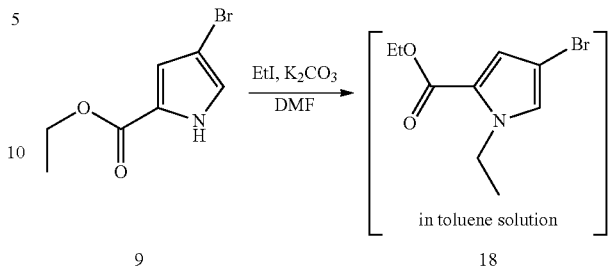

Compound 18 was prepared by treating the pyrrole with ethyl iodide and pulverized potassium carbonate in DMF at 25-30° C. under inert atmosphere. After the reaction was completed, the batch mass was cooled to 15° C. to 20° C. and quenched by slow addition of water then MTBE. The MTBE layer was separated and washed with water. The MTBE layer was distilled to 4 Vol and solvent swapped with toluene. The toluene stream was then taken into the next step.

Example 8

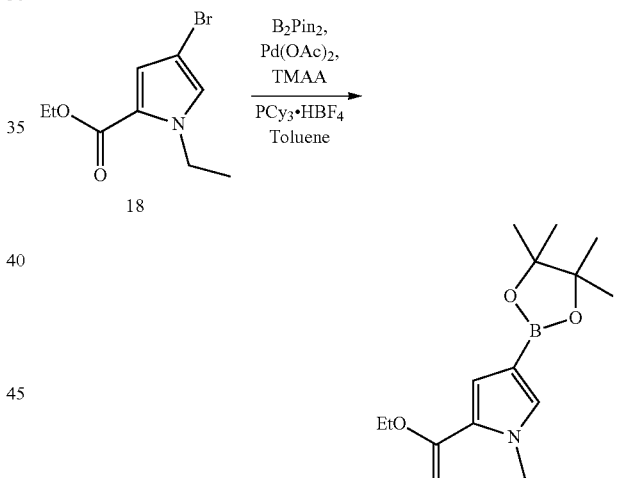

Tetra-methyl ammonium acetate in toluene slurry was heated to 75-80° C. to get a clear solution. The mass was cooled to below 30° C. and pyrrole in toluene and bis(pinacolato) diborane were added. The reactor was inerted by nitrogen purging then the reaction was heated to 75-80° C. A freshly prepared catalyst/ligand complex (0.01 eq of palladium acetate, 0.025 eq of tricyclohexyl phosphino hexafluoroborate and 0.2 eq of tetra methyl ammonium acetate in toluene) was charged under nitrogen atmosphere at RT and stirred for 2 h. The mass was then stirred at 75-80° C. under nitrogen atmosphere. After the reaction was completed, the mixture was cooled below 30° C. and quenched with aq. sodium bisulphate solution. The organic layer was polish filtered through a Celite bed and the filtrate was washed with water. The solvent swapped to ethanol until the

Example 9

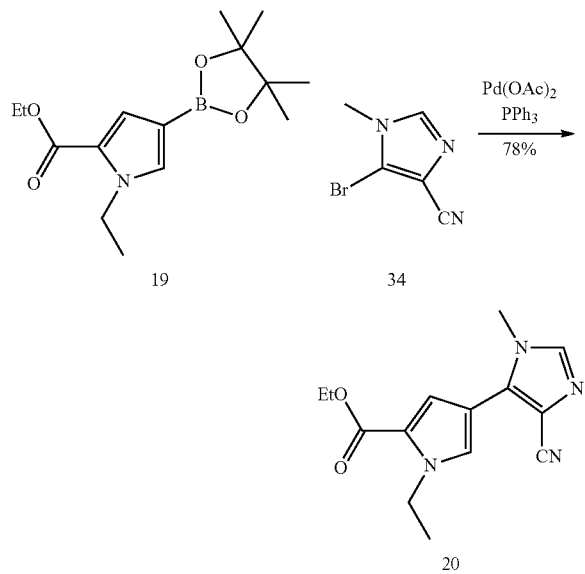

Compound 20 was prepared by treating Compound 19 with Compound 34 in the presence of palladium acetate, triphenyl phosphine and potassium carbonate in dimethyl acetamide with the water mixture as the solvent. Dimethyl acetamide, water, potassium carbonate and the two starting materials were charged into the reactor. The mixture was made inert with nitrogen for 30 min and then charged with freshly prepared catalyst mixture (palladium acetate, triphenyl phosphine and potassium carbonate in dimethyl acetamide). The temperature was raised to 78-83° C. then the mass was stirred at this temperature. After the reaction was completed, the reaction mass was cooled to ambient temperature and purified water was added slowly into the mass for product crystallization. The mass was stirred for a period of 3 h and filtered. The wet cake was washed with purified water and dried in VTD at 50-55° C. under vacuum.

Example 10

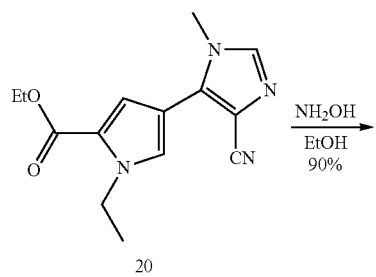

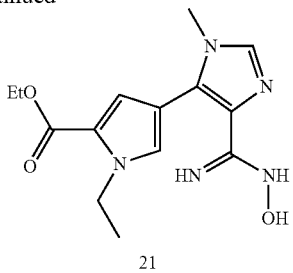

Compound 21 was prepared by treating Compound 20 with hydroxylamine hydrochloride and triethyl amine using ethanol as the solvent. Compound 20 was added into ethanol (15 Vol) and the reaction mass was heated to 38-40° C. Hydroxylamine hydrochloride was charged and stirred for 10 min, then triethyl amine was added slowly at 38-40° C. over a period of 1 h. The above mass was stirred at 38-40° C. until Compound 20 becomes less than 5.0%, typically in about 15 h. After the reaction was completed, the above reaction mass was cooled to ambient temperature (below 30° C.) and filtered. The wet cake was washed with purified water (4 Vol) and dried under vacuum in VTD at 55-60° C.

Example 11

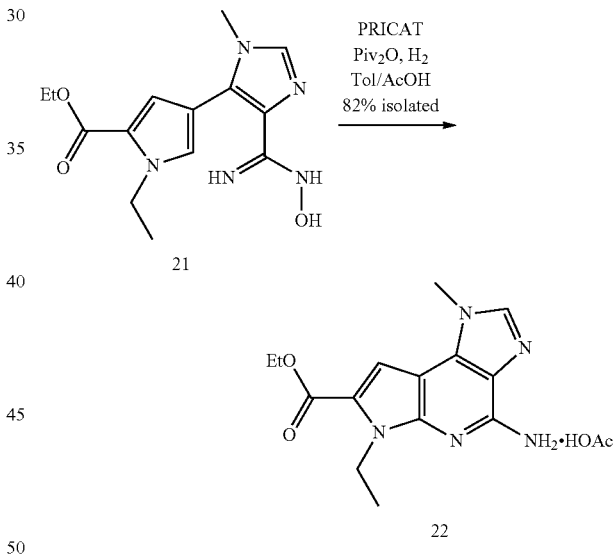

Initially Compound 21 was treated with pivalic anhydride using toluene and acetic acid mixture as solvent under inert atmosphere until Compound 21 becomes less than 3.0% with respect to Compound 21, typically in about 30 min. PRICAT Nickel was then added under nitrogen atmosphere. The reaction mass was inerted with nitrogen for three cycle times and then degassed with hydrogen gas for three cycle times. Following this, 3.0 kg/cm² hydrogen pressure was applied to the reaction mass which was stirred for about 12 h. After the reaction was completed, the reaction mixture was filtered through a sparkler filter. The filtrate was distilled and the solvent exchanged with toluene until the ratio of acetic acid & toluene reaches 1:20. At this time, n-Heptane was charged and cooled to 15° C. Then the product was filtered and the wet cake was dried in VTD at 50-55° C. under vacuum.

Example 12

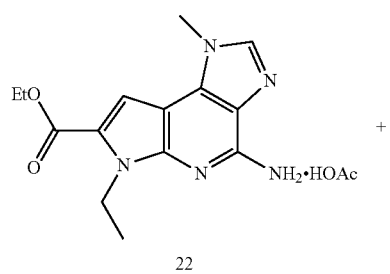

22

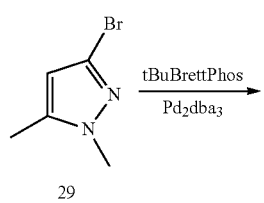

29

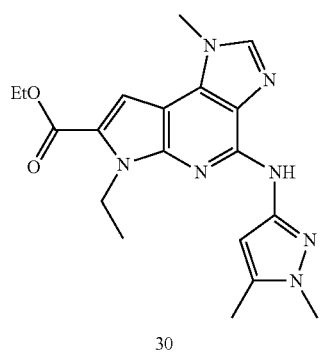

30

Compound 30 was prepared by the coupling of Compound 22 with Compound 29, 3-bromo-1,5-dimethyl-1H-pyrazole in the presence of Tris(dibenzylideneacetone)dipalladium chloroform adduct, t-Brettphos and potassium phosphate in tert-amyl alcohol at 98-103° C. under inert atmosphere. After completion of the reaction (typical level of Int. 9-5% & typical reaction hrs 20 h), the mass was cooled to ambient temperature and t-amyl alcohol (4 Vol) and 20 Vol of water were charged into the reaction mass. The reaction mass was stirred for 15 min. and then phase split. The organic layer was diluted with 10 Vol of MTBE and product was extracted with 20 Vol of 1M methane sulphonic acid. The MSA stream was treated with 15 wt % charcoal to reduce the residual palladium numbers. The filtrate was cooled to below 20° C. and the pH was adjusted to 1.7-1.9 using 1N NaOH for product crystallization and then filtered. The wet cake was washed with purified water (3×5 Vol), followed by methanol (5 Vol). The cake was vacuum dried for 3 h. then the wet cake and dimethyl sulfoxide (20 Vol) were charged into a reactor. The mass was heated to 120-125° C. to get clear solution then the mass was cooled to ambient temperature and stirred for 2 h, then filtered. The wet cake was washed with methanol (3×4.0 Vol) and vacuum dried for 2 h. The wet cake was dried in VTD at below 55° C. under vacuum.

Example 13

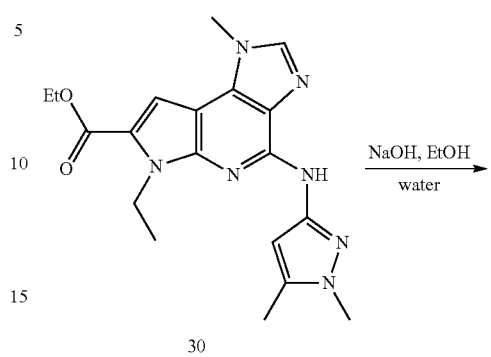

30

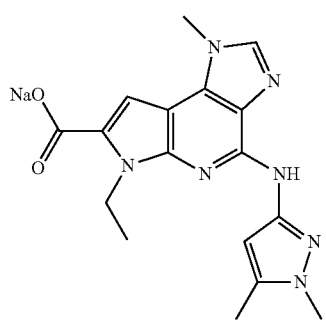

31

Compound 30, ethanol (16.5 Vol), water and aq sodium hydroxide solution were charged into a reactor then the mass was heated to 70-75° C. and stirred until Compound 30 becomes less than 1.0%. After the reaction was completed, the mass was diluted with ethanol for complete product precipitation at 65-75° C. Then the mass was cooled to 50° C. for a period of 1 h and stirred for 1 h at 50° C. The mass was further cooled to 20° C. and stirred for 1 h at 20° C. and then filtered. The wet cake was washed with 5 Vol of 15% aqueous ethanolic solution followed by THF. The wet cake was dried under vacuum at 70-75° C. till LOD comes to less than 5.0%, typically in about 40 h.

Example 14

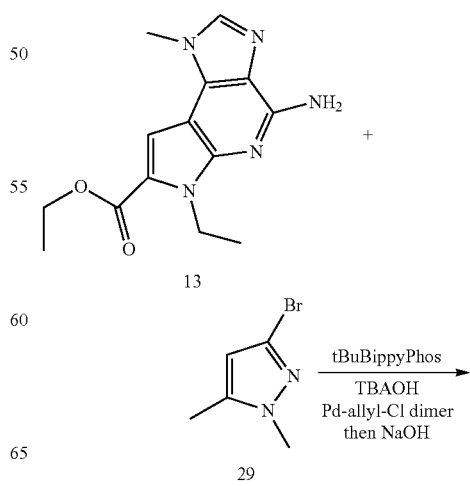

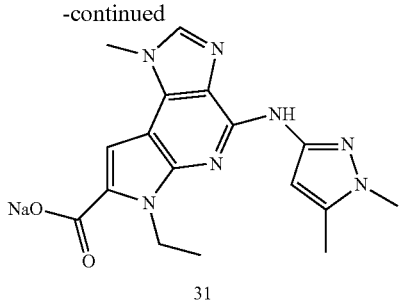

31

In a vessel 36.5 mmol (~42.6 mL) of Compound 29 solution in 2-methyl-2-butanol was combined with 30.7 g (65.1 mmol) tetrabutylammonium hydroxide (55 wt % in water), 8.01 g (27.0 mmol) Compound 13, and 10 mL 2-methyl-2-butanol. The mixture was heated at 70° C. until hydrolysis of Compound 13 was complete (full dissolution, <15 min). The solution was cooled to 60° C. and 1.12 g (2.22 mmol) of tBu-BippyPhos followed by 384 mg (1.028 mmol) allylpalladium chloride dimer (L:Pd=1:1) was added. The mixture was heated to 80° C. and was aged at this temperature for 20 h before cooling to 22° C.

Water was added and the mixture concentrated, a constant volume distillation was then performed to swap to ethanol (40-55° C., 150 mbar). The resulting solution was passed through a 5 micron filter to remove any particulates. The solution was heated to 55° C. and 8.10 mL (40.52 mmol, 1.5 equiv) 5N NaOH (aq) was added dropwise over a 3 h period. Crystals of Compound 31 began to form, and after aging for an additional 1 h, the mixture was cooled to 20° C. over 3 h. After an additional 6 h of aging, crystals were collected on a frit and the cake was washed with 40 mL of 90:10 ethanol: water, followed by 48 mL acetone. After drying at 80° C. in a vacu-oven for 16 h, Compound 31 was collected as an off-white solid (8.89 g, 85%).

Example 15

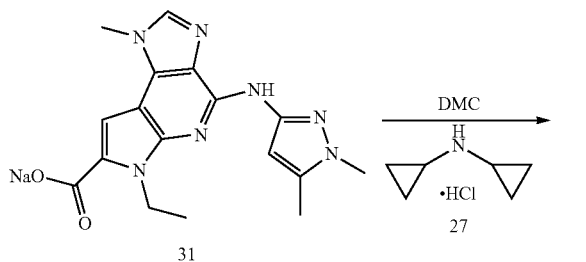

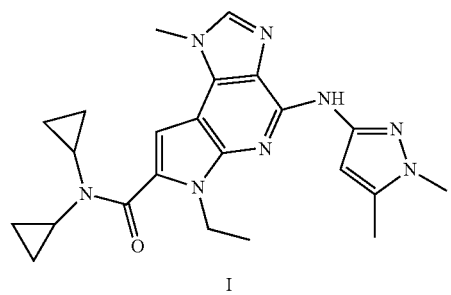

Compound 31 was added into dichloromethane (20 Vol) and cooled to 15-20° C. The reaction mass was charged with DMC in DCM solution (1.4 eq of DMC in 5.0 Vol of DCM). The mixture was stirred until Compound 31 becomes less than 2.0% with respect to the corresponding acid chloride, typically in about 1 h. After completion of the reaction, Compound 27 (1.4 eq) and N,N-diisopropylethyleneamine (3.0 eq) were charged and the mixture was stirred. After completion of the reaction, the mass was quenched with 12 Vol of water then the layers were separated. The organic layer was washed with water and filtered through a celite bed. The filtrate was concentrated to ~6.0 vol and then the mass was cooled to 35° C. To the resulting solution was added THF, followed by seeds of product, then stirred for 3 h. The solvent was swapped with THF until dichloromethane becomes less than 2 wt % (wrt THF). The mass was cooled to ~5 to 0° C. over a period of 2 h and stirred for 2 h. The reaction mass was then filtered under a nitrogen atmosphere. The material was slurried with pre-cooled THF (2*2 Vol) and filtered. The wet cake was dried in VTD at 60° C. under vacuum till LOD becomes <1%, typically in about 20 h.

Example 16

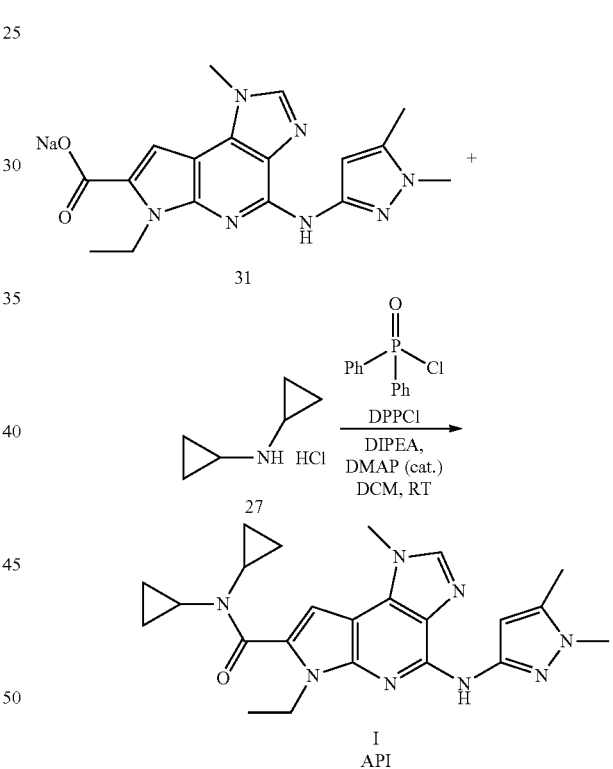

To a slurry of Compound 31 (15.00 g, 40.0 mmol) in dichloromethane (300 ml) was added diphenylphosphinic chloride (12.29 g, 51.9 mmol). The mixture was stirred at room temperature for 2 h and N,N-diisopropylethylamine (16.53 g, 127.9 mmol) was then added and stirred for another 30 min. Compound 27 (6.94 g, 51.9 mmol) and 4-dimethylaminopyridine (0.49 g, 4.0 mmol) were subsequently added and stirred for 16 h until the reaction was completed. The reaction mixture was treated with N-acetyl-L-cysteine (3.26 g, 20.0 mmol) and citric acid (10.10 g, 48.0 mmol) in deionized water (180 ml) for 2 h. After phase split, the dichloromethane phase was washed once with 0.42 N NaOH solution (180 ml) and washed twice with deionized water (180 ml each). The final dichloromethane phase was concentrated (to 90 ml) and acetone (30 ml) was added. The solution was cooled to 35° C. and N-2 form seed of Compound I (150 mg) was added and aged for 1 h. The resulting slurry was solvent-swapped to acetone (DCM<10% v/v), and cooled to 0° C. The solid was filtered and washed with cold acetone and dried to afford 14.69 g (85%) of Compound I (HPLC AP 99.8) as off-white crystals.

What is claimed is:

1. A process for the preparation of Compound I of the formula

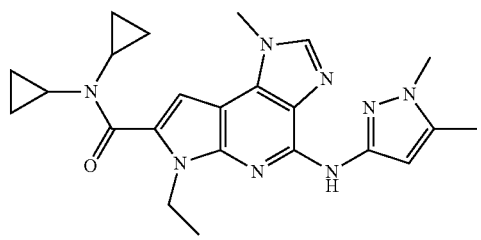
(I)

comprising the steps of
a) reacting Compound 1 of the formula

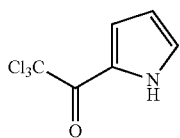
Compound 1 with a halogenating agent, such as NBS, in a suitable solvent to afford Compound 2 of the formula

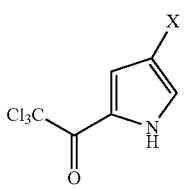
Compound 2 wherein X is Cl, Br or I;
b) reacting Compound 2 with an alcohol to afford Compound 3 of the formula

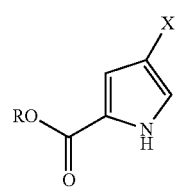
Compound 3 wherein
R is Me, Et, iPr, nPr, nBu, sec-Bu or tBu; and
X is as defined above;
c) subsequently reacting Compound 3 with a nitrating agent to afford Compound 4 of the formula

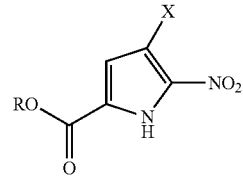
Compound 4 d) reacting Compound 4, first, with an ethylating agent to afford Compound 5 of the formula

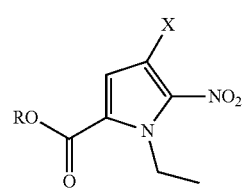
Compound 5 wherein
R and X are as defined above;
and subsequently with a suitably substituted imidazole of the formula,

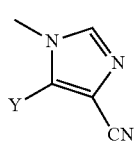
Compound 33 wherein
Y is H, Cl, Br, I or B(OR')$_2$; and
R' is Me, Et, i-Pr, n-Pr, n-Bu, sec-Bu, t-Bu, —(CH$_2$)$_n$ or —C(Me)$_2$C(Me)$_2$-; and
n is 2, 3, 4 or 5;

in the presence of a suitable catalytic metal, a ligand, an inorganic salt and optionally an organic base, to afford Compound 6 of the formula

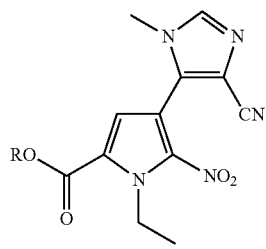
Compound 6 e) which is then reacted with hydrogen in the presence of a suitable catalytic metal and optionally a base, to afford Compound 7 of the formula Compound 7

[Structure: Compound 7 with RO-C(=O)- group]

wherein R is as defined above;
f) which is reacted with Compound 24 of the formula Compound 24

[Structure of Compound 24]

wherein Z is Cl, Br, I, —OP(O)(OR")$_2$ or —OS(O)CF$_3$;
in the presence of a suitable metal, a ligand, and base, to afford Compound 26 of the formula Compound 26

[Structure of Compound 26 with MO-C(=O)- group]

wherein R" is Ph or t-Bu and M is Li, Na, K, Cs, Rb, Mg or Ca;
g) which is reacted with Compound 27 of the formula Compound 27

[Structure: dicyclopropylamine·HCl]

in a the presence of a suitable activator, a suitable solvent, such as DCM, and optionally a base, to afford Compound I.

2. A compound of the formula which is

[Structure with Br, NO$_2$, EtO-C(=O)- pyrrole and Bn$_2$NH]

[Structure with EtO-C(=O)- ... NH$_2$]

[Structure with EtO-C(=O)- ... NH$_2$ ·AcOH] or

[Structure with EtO-C(=O)- ... NH$_2$ ·HCl]

[Structure with NaO-C(=O)- ... NH-pyrazole]

[Structure with NaO-C(=O)- ... NH-pyrazole ·xH$_2$O]

[Structure with NaO-C(=O)- ... NH-pyrazole ·xH$_2$O·EtOH]

3. A method for coupling Compound 11 of the formula

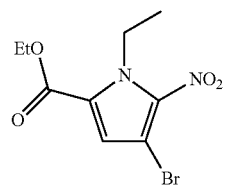 [SMILES: CCOC(=O)c1cc(Br)c([N+](=O)[O-])n1CC]

to Compound 28 of the formula

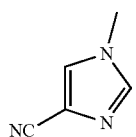

which comprises treating Compound 28 with a suitable palladium source, a phosphine ligand and a suitable potassium source and optionally an organic base to afford Compound 12 of the formula

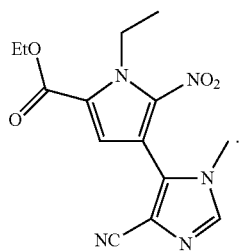 [SMILES: CCOC(=O)c1cc(-c2c(C#N)ncn2C)c([N+](=O)[O-])n1CC]

4. The method of claim 3 wherein the suitable palladium source is a $PdCl_2$ source, or $Pd(OAc)_2$.

5. The method of claim 4 where the suitable potassium source is KOPiv.

6. The method of claim 3 where the suitable phosphine ligand is Xantphos.

7. The method of claim 3 where the optional organic base is Hunig's base.

8. A method for coupling Compound 31 of the formula

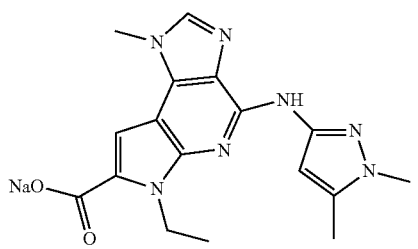

to Compound 27 of the formula

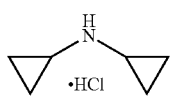

which comprises treating Compound 31 with DPPCl in the presence of base, and subsequently reacting Compound 27 in the presence of DMAP to afford Compound I.

9. A compound of the formula which is

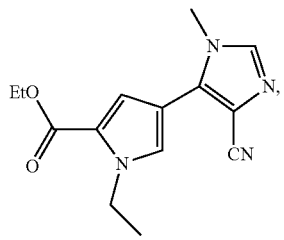

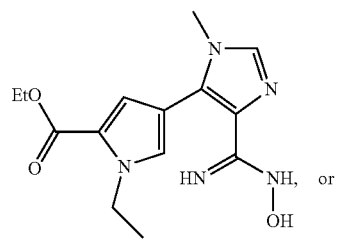

or

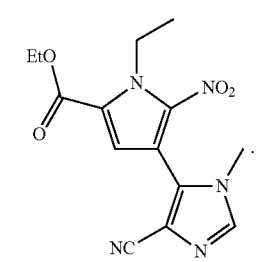

* * * * *